United States Patent [19]

Friedrich et al.

[11] Patent Number: 4,849,401
[45] Date of Patent: Jul. 18, 1989

[54] ALCOHOLS CONTAINING 2-METHYLPHENYL OR 2-METHOXYPHENYL GROUPS, AND FRAGRANCES CONTAINING SAME

[75] Inventors: Wilhelm Friedrich; Helmut Gebauer, both of Munich; Walter Hafner, Eurasburg; Marlies Regiert, Munich, all of Fed. Rep. of Germany

[73] Assignee: Consortium fur elektrochemische Industrie, GmbH, Fed. Rep. of Germany

[21] Appl. No.: 178,272

[22] Filed: Apr. 6, 1988

[30] Foreign Application Priority Data

Apr. 15, 1987 [DE] Fed. Rep. of Germany ....... 3712873

[51] Int. Cl.$^4$ .................................................. A61K 7/46
[52] U.S. Cl. ...................................... 512/25; 568/715
[58] Field of Search .................... 512/20, 25; 568/630, 568/715

[56] References Cited

U.S. PATENT DOCUMENTS 4,512,918 4/1985 Wieger et al. ....................... 512/20

FOREIGN PATENT DOCUMENTS 0059373 9/1983 European Pat. Off. ............ 568/630

OTHER PUBLICATIONS

Royals et al., "J. Organic Chem.", vol. 23, (1958), pp. 1437-1443.

Primary Examiner—Werren B. Lone
Attorney, Agent, or Firm—Collard, Roe & Galgano

[57] ABSTRACT

The invention discloses compounds of the general formula

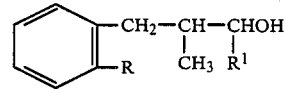

in which
R represents a methyl radical or a methoxy radical when $R^1$ is a hydrogen atom; or
R represents a methyl radical when $R^1$ is a methyl radical.

The compounds of the invention are useful as fragrances.

3 Claims, No Drawings

ALCOHOLS CONTAINING 2-METHYLPHENYL OR 2-METHOXYPHENYL GROUPS, AND FRAGRANCES CONTAINING SAME

The present invention generally relates to alcohol compounds which contain 2-methylphenyl or 2-methoxyphenyl groups, and their use as fragrances. More particularly, the present invention relates to 2-methylphenyl- or 2-methoxyphenyl-containing alcohols which have the beneficial properties of oakmoss perfumes, but without the undesirable or otherwise toxic characteristics of such perfumes.

Oakmoss perfumes are known, but such perfumes are mostly phenol derivatives, such as 3-methyl-5-methoxy-phenol, having known harmful phenolic properties, such as causticity or irritant action and discoloration.

Furthermore, 2-methyl-3-(2-methylphenyl)-propan-1-ol is known from *J. Indian Chem. Soc.*, Vol. L, September 1973, but a use for this compound was not given in this publication.

It is therefore an object of the present invention to provide fragrances which have an oakmoss character, high stability and none of the harmful properties generally associated with oakmoss perfumes, such as causticity, irritant action or discoloration.

The foregoing and related objects are achieved by the present invention which relates to compounds of the formula

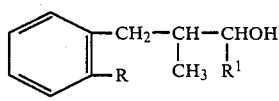

wherein R denotes a methyl or methoxy radical when $R^1$ is a hydrogen radical, and R denotes a methyl radical when $R^1$ is a methyl radical, and 2-methyl-3-(2-methylphenyl)-propan-1-ol is excluded.

A process for the preparation of 2-methyl-3-(2-methylphenyl)-propan-1-ol and 2-methyl-3-(2-methoxyphenyl)-propan-1-ol is also provided and comprises the steps of:

(a) reacting 2-methylbenzaldehyde or 2-methoxybenzaldehyde with propionaldehyde in the presence of bases, and (b) hydrogenating the reaction product from (a).

The benzaldehyde and propionaldehyde used as starting compounds are known substances.

The reaction in step (a) preferably takes place using alkali metal hydroxides, in particular sodium hydroxide or potassium hydroxide, at temperatures of, preferably, −5° to 80° C. in polar solvents, such as alcohols, for example, methanol or ethanol. The reaction product from step (a) is then hydrogenated using reduction catalysts, such as palladium on activated charcoal or Raney nickel, and hydrogen, and finally separated into the aldehyde or alcohol by fractional distillation.

A further process for the preparation of 2-methyl-3-(2-methylphenyl)-propan-1-ol or 2-methyl-3-(2-methoxyphenyl)-propan-1-ol comprises the steps of:

(a1) reacting 2-methylbenzyl chloride or 2-methoxybenzyl chloride with diethyl methylmalonate, (b1) thermally decarboxylating the reaction product from (a1) after hydrolysis, and (c1) hydrogenating the reaction product from (b1).

The benzyl chlorides and diethyl methylmalonate used are known compounds. The reaction in step (a1) preferably takes place at temperatures of 70° to 120° C. in the presence of a base, such as sodium hydroxide or potassium hydroxide, and thermal decarboxylation in step (b1) is carried out preferably at 120° to 150° C. The acid obtained is reacted, optionally, after esterification using alcohols, such as methanol or ethanol, with hydrogenating agents, usch as lithium aluminum hydride or hydrogen, in the presence of a catalyst.

A process for the preparation of 3-methyl-4-(2-methylphenyl)-butan-2-ol comprises reacting 2-methylbenzyl chloride with methyl ethyl ketone in an organic-/alkaline two-phase system in the presence of a phase-transfer catalyst.

2-Methylbenzyl chloride and methyl ethyl ketone are known compounds. Methyl ethyl ketone is preferably employed in excess. The organic/alkaline two-phase system is formed from the reaction components, and also, optionally, an organic water-immiscible inert solvent and a 5–50% strength aqueous solution of an alkali metal hydroxide or, in solid form, an alkali metal hydroxide or alkali metal carbonate. Examples of alkali metal hydroxides are sodium hydroxide or potassium hydroxide. Examples of the phase-transfer catalysts employed are crown ethers, quaternary ammonium salts or quaternary phosphonium salts in amounts of 0.5–5 mole-% relative to benzyl chloride. The reaction product from this reaction is then reduced to 3-methyl-4-(2-methylphenyl)-butan-2-ol in a manner which is known per se using reducing agents, such as sodium borohydride, lithium aluminum hydride or hydrogen, and a catalyst. The examples which follow hereinafter further detail such synthesis processes.

The invention further relates to the use of the compounds, according to the invention, as fragrances. In this case, 2-methyl-3-(2-methylphenyl)-propan-1-ol is not excluded.

The fragrances according to the invention exhibit an oakmoss character and high chemical and physical stability. Due to their stability, they have a very broad range of applications. Besides use in perfumery, they are also suitable for perfuming soaps and detergents, textiles, plastic products and the like.

The invention will now be explained in greater detail by reference being made to the following examples. It should, however, be understood that the following examples are provided for purposes of illustration only and are not intended as a definition of the scope or limits of the present invention.

EXAMPLE 1

2-Methyl-3(2-methoxyphenyl)-propan-1-ol

While flushing with argon, 6.5 g of KOH were dissolved in 200 ml of ethanol (95% strength), and the solution was cooled to 4° C. 98 g of 2-methoxybenzaldehyde were then added, and 45 g of propionaldehyde were added dropwise over the course of 4.5 hours. The reaction temperature was kept at 8°–9° C. After a post-reaction time of 15 minutes, ice, water and ether were added and the organic phase was separated off. It was washed by shaking four times with 200 ml of water in each case and distilled through a 19 cm packed column containing glass coils. After removal of the solvent and preliminary fraction, a fraction (88 g) containing 94% of 2-(2-methoxybenzylidene)-propionaldehyde was obtained from 86°–92° C. at 0.07 mbar. 87 g of this substance, 150 ml of ethanol and 10 g of Raney nickel were heated at 130° C. for 14 hours in a shaken autoclave under a hydrogen pressure of 100 bar. After removal of the catalyst and solvent, the mixture was distilled through the above-mentioned column. 70 g of 2-methyl-3-(2-methoxyphenyl)-propan-1-ol were obtained at 98° C./0.13 mbar.

Odor note: earthy-phenolic, comparable to the characteristics of roots and oakmoss.

EXAMPLE 2

2-Methyl-3-(2-methylphenyl)-propan-1-ol 220 g of 2-methylbenzyl chloride, 320 g of diethyl methylmalonate, 320 g of potassium carbonate, 13 g of potassium iodide and 10 g of 18-crown-6 were stirred at 90° C. for 12 hours in 1 liter of toluene. The cooled mixture was stirred with 800 g of ice in water, and the aqueous layer was separated off and extracted once with ether. The combined organic layers were washed by shaking three times with 400 ml of water in each case. The solvent and unreacted diethyl methyl malonate were then removed by distillation, partly under reduced pressure. The residue (413 g) was hydrolyzed using 540 g of 25% strength NaOH with addition of a spatula tip of tetradecyltrimethylammonium bromide (14 hours reflux). During this procedure, liberated ethanol was removed by distillation and a little water was added.

The mixture was then acidified using concentrated hydrochloric acid, and the organic phase was taken up on xylene and slowly heated to reflux over several hours for decarboxylation. The xylene was subsequently removed again by distillation, and the 2-methyl-3-(2-methylphenyl)-propionic acid remaining was esterified azeotropically using ethanol and cyclohexane. The ester was distilled through a 20 cm packed column (220 g, boiling point 68°–71° C. at 0.1–0.2 mbar).

1.2 liters of dry tetrahydrofuran were introduced into a 2 l four-necked flask, 38 g of lithium aluminum hydride were added under argon, and a mixture of 200 g of the above ester with 200 ml of ether was added dropwise with ice cooling. After a post-reaction time of 2 hours at room temperature, the batch was poured into water and acidified using hydrochloric acid, and the layers were separated. The aqueous phase was extracted twice with ether, and the combined organic phases were washed by stirring with sodium carbonate solution and distilled (20 cm packed column containing glass coils). 148 g of 2-methyl-3-(2-methylphenyl)-propan-1-ol of boiling point 80° C. at 0.13 mbar were obtained.

Odor note: oakmoss and vetiver.

EXAMPLE 3

3-methyl-4-(2-methylphenyl)-butan-2-ol 56 g of KOH, 56 ml of water, 10 g of 18-crown-6 and 5 g of KI were warmed to 75° C. with 200 ml of toluene with exclusion of air. A mixture of 100 g of 2-methylbenzyl chloride and 100 g of methyl ethyl ketone was added dropwise over 30 minutes with vigorous stirring, and the mixture was stirred at 85° C. for 11 hours. The phases were then separated, and the organic layer was washed by shaking with water and distilled through a short packed column. After removing the solvent and the preliminary fraction, 29 g of 3-(2-methylbenzyl)-butanone were obtained at 54°–55° C./0.07 mbar. 25 g of this compound was stirred with 3 g of $NaBH_4$ in 100 ml of ethanol, initially for 2 hours at 25° C., then for a further 2 hours at the reflux temperature. After the reducing agent and solvent had been removed, the reaction product was distilled through a short Vigreux column. 15.5 g of 3-methyl-4-(2-methylphenyl)-butan-2-ol were obtained from 64°–67° C./0.07 mbar.

Odor note: oakmoss, with a sweet-powdery component.

While only several embodiments and examples of the present invention have been shown and described, it will be obvious to those skilled in the art that many changes and modifications may be made thereunto, without departing from the spirit and scope of the invention.

What is claimed is:

1. A compound of the formula:

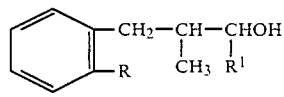

wherein
R represents a methoxy radical when $R^1$ is a hydrogen atom; or
R represents a methyl radical when $R^1$ is a methyl radical.

2. A fragrance composition comprising a compound of the formula:

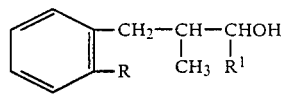

wherein
R represents a member selected from the group consisting of a methyl radical and a methoxy radical, when $R^1$ is a hydrogen atom; or
R represents a methyl radical when $R^1$ is a methyl radical.

3. A process for the preparation of a fragrance composition, comprising the step of:
adding, as an active ingredient of said fragrance composition, a compound of the formula

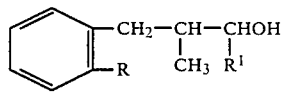

wherein,
R represents a member selected from the group consisting of a methyl radical and a methoxy radical, when $R^1$ is a hydrogen atom, or
R represents a methyl radical where $R^1$ is a methyl radical, to a carrier substance.

* * * * *